United States Patent [19]

King et al.

[11] Patent Number: 5,059,811
[45] Date of Patent: Oct. 22, 1991

[54] TURBIDIMETER HAVING A BAFFLE ASSEMBLY FOR REMOVING ENTRAINED GAS

[75] Inventors: Karl L. King, Brown Deer; Bruce W. Weiss, Whitefish Bay; Robert W. Endl, Johnson Creek, all of Wis.

[73] Assignee: Great Lakes Instruments, Inc., Milwaukee, Wis.

[21] Appl. No.: 574,998

[22] Filed: Aug. 30, 1990

[51] Int. Cl.[5] ........................................... G01N 15/06
[52] U.S. Cl. ..................................... 250/573; 250/576; 356/442
[58] Field of Search ........................ 250/573, 575, 576; 356/442, 440, 441

[56] References Cited

U.S. PATENT DOCUMENTS

| | | | |
|---|---|---|---|
| 1,883,116 | 10/1932 | Tomlinson | 250/573 |
| 3,557,376 | 1/1971 | Senyk | 250/573 |
| 3,775,013 | 11/1973 | Simms | 356/208 |
| 3,849,002 | 11/1974 | Hach | 356/103 |
| 3,953,136 | 4/1976 | Hach | 356/181 |
| 4,198,161 | 4/1980 | Larson | 356/339 |
| 4,366,384 | 12/1982 | Jensen | 250/575 |
| 4,900,152 | 2/1990 | Wiegleb | 250/576 |
| 4,989,974 | 2/1991 | Anton et al. | 250/576 |

FOREIGN PATENT DOCUMENTS 1368302 9/1974 United Kingdom .

Primary Examiner—David C. Nelms
Assistant Examiner—Que T. Le
Attorney, Agent, or Firm—Quarles & Brady

[57] ABSTRACT

A turbidimeter includes a housing having a cavity with an inlet through which the fluid enters the bottom of the cavity, and an outlet through which the fluid exits the top of the cavity. A removable baffle assembly is located within the cavity between the inlet and outlet. The baffle assembly is formed by three vertical plates spaced from each other and extending across substantially the entire cross sectional area of the cavity. The first plate defines a first passage near the top of the cavity through which all the fluid entering the cavity must flow. The second and third walls define a second passage near the top of the cavity through which gas bubbles entrained in the fluid travels to the outlet. A third passage is defined between the first wall and the outlet and a mechanism is provided for measuring the turbidity of the fluid flowing through the third passage. A calibration device formed by a block of glass ceramic material is insertable in the third passage to simulate a known turbidity fluid.

22 Claims, 4 Drawing Sheets

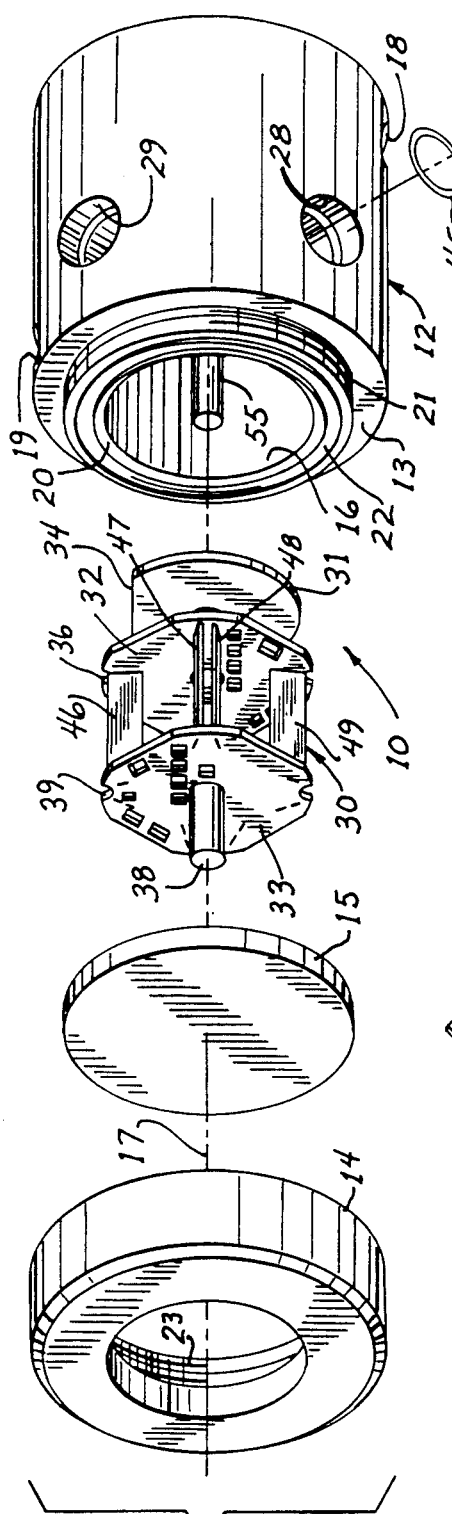
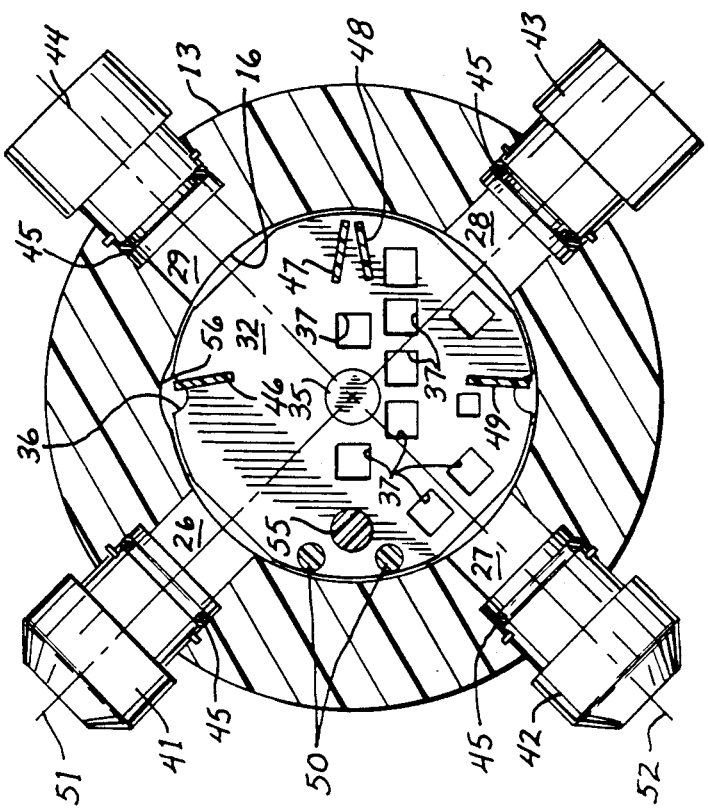

TURBIDIMETER HAVING A BAFFLE ASSEMBLY FOR REMOVING ENTRAINED GAS

BACKGROUND OF THE INVENTION

The present invention relates to apparatus for measuring the turbidity of fluids; and particularly to optical turbidimeters which utilize light emitters and detectors to sense the turbidity.

Turbidity is an optical characteristic of a fluid that is related to the presence, nature and amount of suspended matter or particles which scatter light in an otherwise pure fluid. Turbidity may be sensed by instruments commonly known as turbidimeters which measure the characteristic in terms of the amounts of light which are transmitted directly through and scattered by the fluid.

U.S. Pat. No. 3,775,013 discloses a turbidimeter which utilizes two light sources and two detectors in which each detector is aligned with a different light source. Alternately each light source is energized and the amounts of light detected by the aligned and unaligned detectors are compared. The detector signals produced when each light source is energized are processed to derive a turbidity value, as defined by the U.S. Environmental Protection Agency. Such photoelectric instruments permit turbidity measurements to be conducted on static fluids or those which flow continuously between the emitters and detectors.

The presence of gas bubbles entrained in the fluid affects the optical transmissivity, and therefore the turbidity measurement. As a consequence, gas bubble removal is important to the accuracy of the instrument. Various mechanisms, such as the one described in U.S. Pat. No. 3,849,002, have been proposed to remove air bubbles from the fluid flow before reaching the section of the instrument at which the turbidity is measured.

A further factor affecting instrument accuracy, particularly at low turbidity values, is stray light that is scattered from the various internal surfaces of the measuring cavity. Such stray light produces an erroneous indication of turbidity because it is not caused by light scattered from material suspended in the measuring zone.

Another factor affecting instrument accuracy is the calibration of its circuitry which transforms the detector signals into the turbidity value. Conventional techniques for performing such calibration involved introducing a fluid having a known turbidity into the sensing region. The instrument then was operated while the circuitry was adjusted to produce a turbidity measurement which coincided with the known turbidity of the fluid. The reference fluids must be prepared carefully to insure a uniform, desired turbidity. A commonly used reference fluid called Formazin contains a known carcinogen. In addition, such reference fluids often have a relatively short "shelf life" after which the suspended particles settle or agglomerate resulting in a non-uniform fluid. Thus a certain level of care must be taken during the calibration process to insure that the reference fluid in fact has the known turbidity.

SUMMARY OF THE INVENTION

A turbidimeter comprises a housing within which is defined a cavity through which a fluid can flow to be measured. An inlet is located near one end of the cavity and an outlet is positioned near another end. A baffle assembly, located within the cavity, has a first means for directing substantially all the fluid from the inlet into an upper region of the cavity. The baffle assembly creates a first passage through the upper region to the outlet for any gas entrained in the fluid. A second passage is created for fluid without entrained gas to flow from the upper region through a turbidity sensing zone to the outlet. A mechanism is provided to measure the turbidity of the fluid flowing in the sensing zone.

In the preferred embodiment, the first means for directing comprises a first wall extending vertically in the lower region of the cavity and defining another passage in the upper region for the fluid to flow from one side of the first wall to another side. Second and third walls are spaced different distances from the first wall and extend vertically in both the upper and lower regions of the cavity. Gaps between the housing and the tops of the second and third walls define the first passage. Apertures through the second and third walls provide the second passage with the turbidity sensing zone located between those walls.

The baffle assembly also has means to block stray light from entering the detectors. In the preferred embodiment, rectangular vanes are placed between the second and third walls of the baffle assembly. When the baffle assembly is inserted into the measuring cavity, each of the detectors has two associated vanes, each vane being disposed at an acute angle to a line from the detector to the opposite light source. One edge of each vane is in close proximity to the cavity wall, with the opposite edge in the sensing cavity. The inner edges of the two vanes associated with each detector are separated from each other, allowing light from the turbidity sensing zone to reach the detector.

A novel device for calibrating the turbidimeter includes a calibration standard formed of glass ceramic composite material. During the calibrating process, the calibration standard is placed in the turbidity sensing zone to simulate a fluid having a known turbidity against which the measuring mechanism results can be compared until the mechanism is adjusted to produce the correct turbidity measurement.

An object of the present invention is to provide a turbidimeter which incorporates a mechanism for removing gas entrained in the fluid before the fluid reaches a sensing zone.

Another object is to provide a turbidimeter which incorporates a mechanism for blocking stray light from entering the light detectors.

A further object is to provide an easy to use turbidity standard for calibrating a turbidimeter.

BRIEF DESCRIPTION OF THE DRAWINGS

FIG. 2 is an exploded view of the turbidimeter;

FIGS. 3, 4 and 5 are cross sectional views of the turbidimeter along the correspondingly numbered lines indicated in FIG. 1;

DETAILED DESCRIPTION OF THE INVENTION

Figure 1:
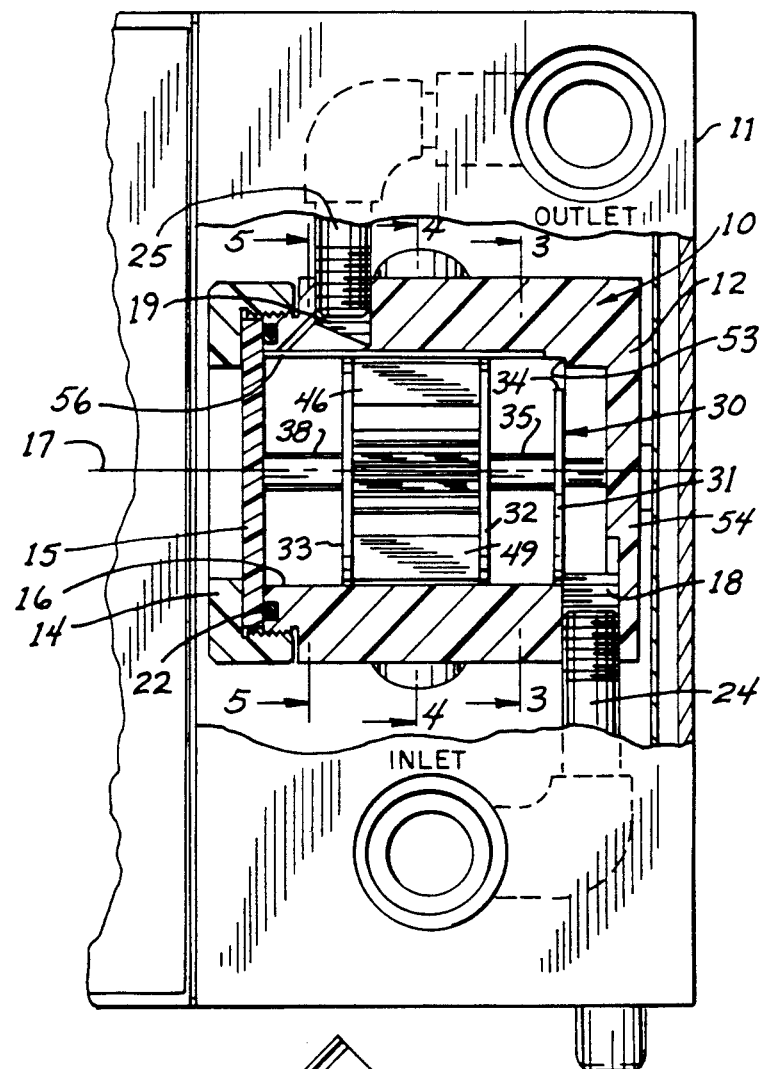
FIG. 1 is a partially cut away diagram of a cabinet which encloses a turbidimeter according to the present invention.

With initial reference to FIGS. 1 and 2, a turbidity sensor 10 is mounted within a cabinet 11. The sensor 10 includes a housing 12 which in the preferred embodiment has a cylindrical shape. The housing 12 consists of a main body 13, annular end cap 14 and a flat, circular end plate 15.

The main body 13 has a cylindrical cavity 16 with a longitudinal axis 17. An inlet opening 18 extends through the main housing near one end of the cavity 16 and an outlet opening 19 extends through the main body near the other end of the cavity. Pipe threads are cut in the housing surfaces forming the inlet and outlet openings 18 and 19 to accept pipe fittings 24 and 25, respectively. The other end of the cavity 16 opens through an annular projection 20 that has external threads 21 on its outer circumferential surface. An O-ring 22 lies within a grove on the planar end surface of projection 20 to provide a fluid tight seal between the main body 13 and the end plate 15. The inner curved surface of the annular end cap 14 has internal threads 23 which engage the external threads 21 on the main body projection 20 when the housing 12 is assembled. This engagement holds the end plate 15 tightly against the main body 13 sealing the cavity 16.

Four radial apertures 26, 27, 28 and 29 extend through the cylindrical main body 13 as illustrated in FIG. 4. These apertures preferably lie in a common plane orthogonal to the longitudinal axis 17 of the cavity 16 and between the inlet and outlet openings 18 and 19. The radial apertures 26-29 are spaced at substantially 90° increments around the cavity 16. Specifically, the first radial aperture 26 is centered on a common first radial axis 51 with the third radial aperture 28. Similarly, the second and fourth radial apertures 27 and 29 are centered on a second radial axis 52 which is substantially perpendicular to the first radial axis 51. A first light emitter 41 is located within the first radial aperture 26 and emits a beam of light through the cavity along the first radial axis 51. A second light emitter 42 is mounted with the second radial aperture 27 and emits a beam of light through the cavity along the second radial axis 52. A first light detector 43 is positioned within the third radial aperture 28 and a second light detector 44 is mounted within the fourth radial aperture 29. Fluid tight seals are provided between the main body 13 and each of the light emitters and detectors 41-44 by O-rings 45.

As shown in FIG. 1, the turbidity sensor 10 is mounted within the cabinet 11 at an orientation in which the longitudinal axis 17 of the cavity 16 is substantially horizontal. The turbidimeter housing 12 is further positioned so that the inlet opening 18 is at the bottom of the cavity 16 and the outlet opening 19 is at the highest port of the cavity. The significance of this orientation will become apparent from a description of the turbidimeter operation subsequently herein.

Located within the cavity 16 is a baffle assembly 30 formed by three plates 31, 32 and 33. The first plate 31 has a generally D-shape with a horizontal straight edge 34 at the upper portion of the plate in the assembled turbidimeter, as illustrated in FIGS. 1, 2 and 3. The curved edge of the first plate 31 has a radius substantially equal to the radius of the cylindrical cavity 16 so that the curved edge of the first plate abuts the inner surface of the cavity. The first plate is fixedly attached near its center to one end of a first spacer 35.

With reference to FIGS. 1, 2 and 4, the other end of the first spacer 35 is attached near the center of the second baffle plate 32. The second plate 32 has a generally square shape with rounded corners conforming to the cylindrical surface of the cavity 16. The upper edge of the second plate 32 contains an indentation 36 providing a gap between the surface of the cavity and the second plate. A number of apertures 37 extend through a lower portion of the second plate. The apertures 37 permit fluid which is introduced into the cavity 16 via inlet opening 18 to flow through the second plate 32, as will be described.

The second and third plates 32 and 33 are spaced from one another by four slat-like vanes 46-49 and two cylindrical posts 50. The ends of the vanes 46-49 are attached to the second and third plates. When the baffle assembly 30 is positioned within the sensor 10 as shown in FIG. 4, the first vane 46 lies near the curved surface of chamber 16 between the first and third radial apertures 26 and 28 at an acute angle to the second radial axis 52. The first vane 46 blocks light produced by the first emitter 41 from traveling in a straight path to the second detector 44. Thus the only way that the second detector 44 can receive light from the first emitter 41 is due to scattering of the light by fluid flowing through the cavity. The second and third vanes 47 and 48 are positioned between the second and third plates 32 and 33 approximately 90° around the edge of the plates from the first vane 46. This positioning of the second and third vanes 47 and 48 places them between the third and forth radial apertures 28 and 29 in the main body. In this location these latter two vanes prevent light from being reflected from the surface of one of the detectors 43 or 44 directly on to the other detector. The fourth vane 49 is located adjacent the cavity surface between the second and third radial apertures 27 and 28 at an acute angle to the first radial axis 51 when the baffle assembly 30 is within cavity 16. The fourth vane 49 blocks light from traveling in a straight line between the second emitter 42 and the first detector 43. Thus, the only way the first detector 43 can receive light from the second emitter 42 is due to scattering of the light by fluid flowing through the cavity. The four vanes 46-49 act as blinders by narrowing the angles of view of the detectors 43 and 44. This limits the amount of stray light reflected by the surfaces of housing 12 and baffle 30 which can reach the detectors.

Figure 5:
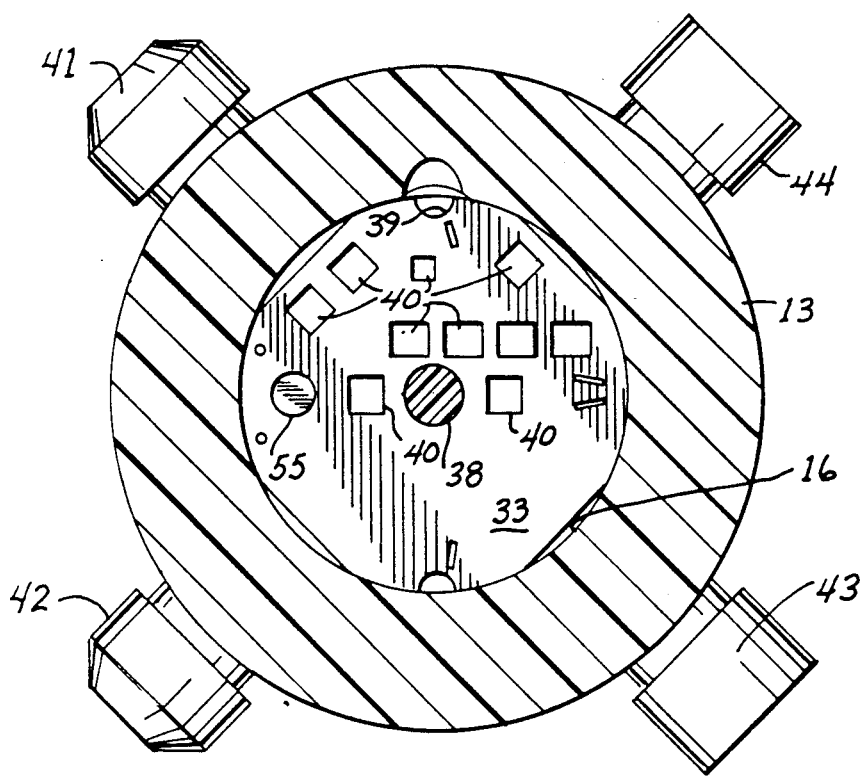

Referring to FIGS. 1 and 5, the third plate 33 is spaced from the housing end plate 15 by a second spacer 38. The third plate 33 has a generally square shape with the corners rounded to conform with the curved surface of cavity 16. An indentation 39 is located in the upper most portion of the edge of the third plate. A series of apertures 40 extend through the upper portion of the third plate 33.

A cylindrical retainer post 55 is fixedly attached to end wall 54 of the main body 13 and extends within the cavity 16 parallel to but offset from longitudinal axis 17. Each of the baffle plates 31-33 has a circular aperture through which the retainer post 55 extends when the baffle assembly is inserted into the cavity 16. The engagement of the retainer post 55 with the plates prevents the baffle assembly 30 from rotating within the cavity due to the force of fluid flowing therethrough. The baffle assembly 30 is restricted from moving longitudinally within the cavity 16 by the second spacer 38 abutting end plate 15 and by the first plate 31 abutting a ridge 53 extending around the inner surface of the cavity near inlet opening 18. The components of the baffle assembly 30, the inner surfaces of housing 12 and retainer post 55 all are colored black to reduce their reflectivity.

When the turbidity sensor 10 is coupled to a plumbing system, fluid flows through the inlet opening 18 into the cavity 16 exiting through outlet opening 19. As shown in FIG. 1, the fluid enters the cavity between the first baffle plate 31 and the end wall 54. Because the curved edge of the first plate 31 conforms to the cavity surface, the fluid can flow around the first plate substantially only between the straight edge 34 of the plate and the main body 13 at the upper region of the cavity. Thus the first plate 31 forces the incoming fluid to the upper region of the cavity, i.e. the region above the upper edge 34 of the plate. Since gas bubbles entrained in the fluid are lighter than the fluid, the bubbles flow along a passage created in the upper region between indentation 36 in the second plate 32 and a grove 56 which extends in the main body 13 longitudinally along the upper cavity surface. The passage continues along this grove 56 and through the indentation 39 in the second baffle plate 32 until it reaches the outlet opening 19. The gas bubbles carried by the fluid will flow across the upper region of the cavity and not intersect the radial axes on which the light emitters and detectors 41-44 are located. As a result, the gas bubbles will not interfere with the optical sensing of the fluid turbidity.

However, the cross sectional area of the passage at the upper region of the cavity is relatively small as compared to the size of the inlet and the combined cross sectional areas of the apertures 37 in the second plate 32. As a result, most of the flow volume will be forced downward in a section of the cavity between the first and second plates and through apertures 37. Alternatively, indentations can be provided in edges of the lower half of the second plate 32 to accommodate the fluid flow The fluid flows from the apertures 37 in the second baffle plate 32 in a upward angular direction to the apertures 40 in the third plate 33. By vertically offsetting the apertures 37 and 40 in the second and third baffle plates 32 and 33 the fluid is directed through the central region of the cavity formed between the two plates and through the beams of light produced by the emitters 41 and 42. This central region forms the turbidity sensing zone. The baffle assembly 30 performs the functions of removing entrained gas from the fluid flow before the sensing zone of the turbidimeter and directing the flow of fluid that is substantially gas bubble free through that sensing zone.

Figure 6:
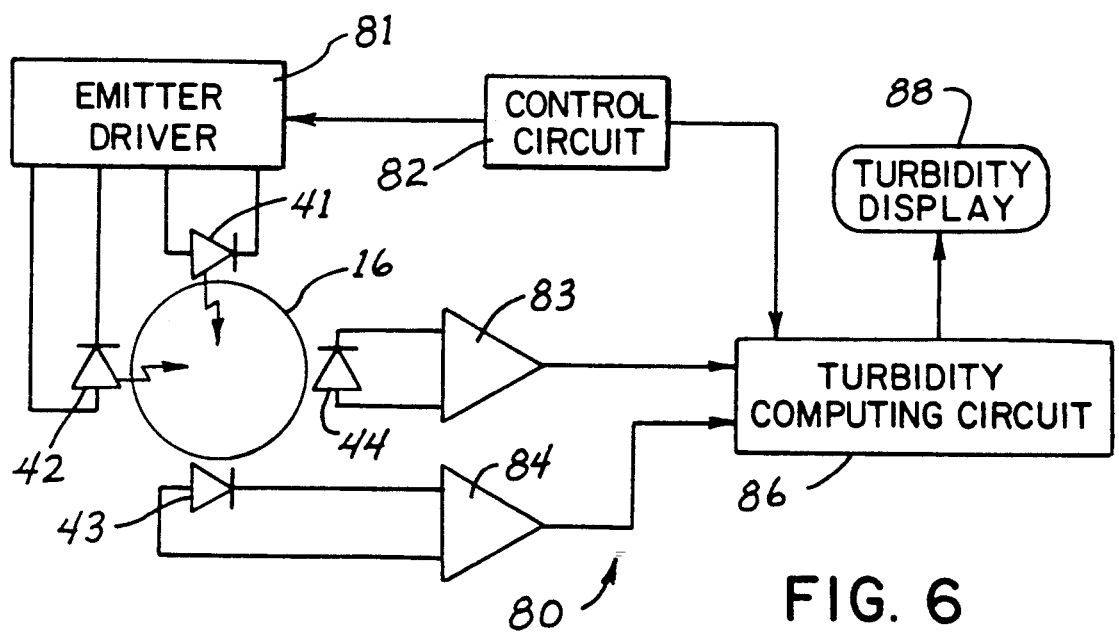
FIG. 6 is a block diagram of the turbidimeter signal processing circuitry.

As shown in FIG. 6, the light emitters 41 and 42 and detectors 43 and 44 are connected to a circuit 80 for deriving a turbidity value based on signals from detectors 43 and 44. The light emitters 41 and 42 are alternately energized by an emitter driver 81 in response to a signal from control circuit 82. The signals from the detectors 43 and 44 are coupled by preamplifiers 83 and 84 to a turbidity computing circuit 86. From the two input signals, the turbidity computing circuit calculates a turbidity value in a manner similar to that described in U.S. Pat. No. 3,775,013. This value is presented on display 88.

Figure 7:
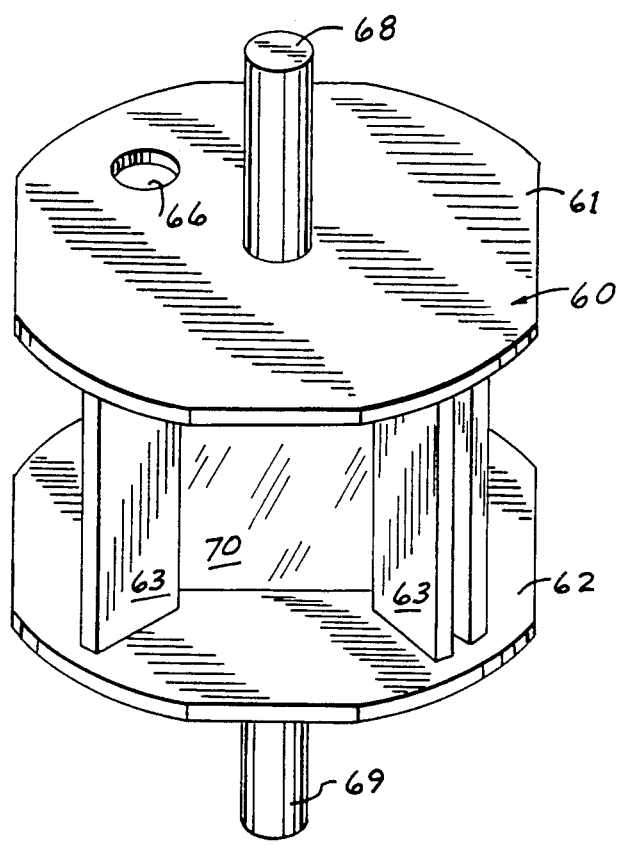
FIG. 7 is a isometric view of a device for calibrating the turbidimeter.
Figure 8:
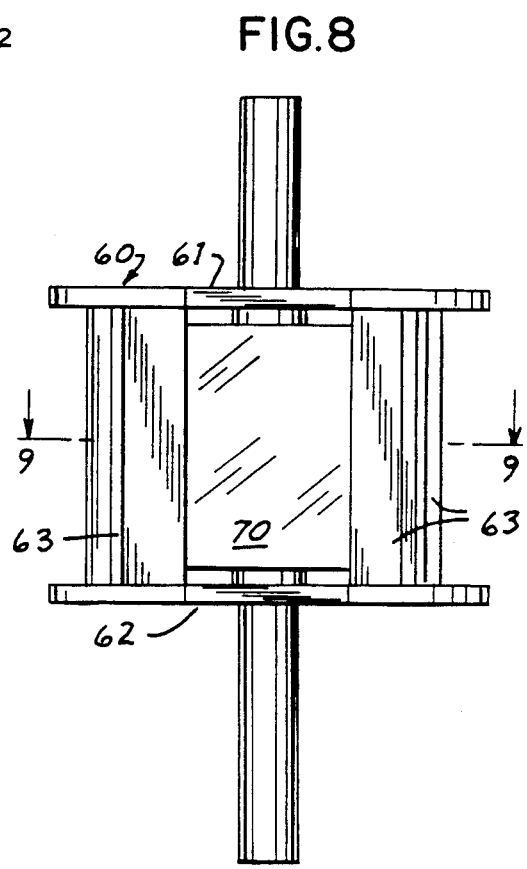
FIG. 8 is a plane view of the calibration device.
Figure 9:
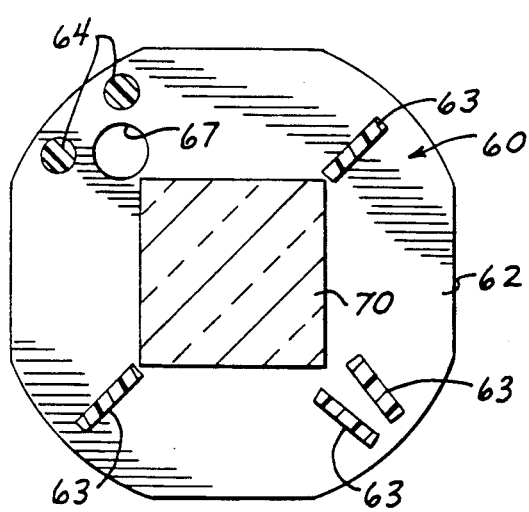
FIG. 9 is a cross sectional view taken through the calibration device.

In order for the signal processing circuit 80 to convert the light intensity sensed by detectors 43 and 44 into a correct turbidity measurement, the circuitry must be calibrated. The present turbidimeter also provides an improved method of calibration compared to previous methods which used a fluid having a known turbidity. A novel calibration device used in this process is illustrated in FIGS. 7-9. To calibrate the instrument, the baffle assembly 30 is removed from the turbidimeter 10 and the calibration device 60 is inserted in its place. The calibration device 60 is similar to the baffle assembly 30 in that it has two plates 61 and 62 spaced apart by four vanes 63 and rods 64. The plates 61 and 62 have a shape which conforms to the cross section of the cavity 16. The vanes 63 and rods 64 of the calibration device 60 extend between the two plates 61 and 62 in positions similar to the vanes 46-49 of the baffle assembly 30 and perform similar functions. Each calibration device plate 61 and 62 has an aperture 66 and 67, respectively, for receiving the retainer post 55 when the calibration device is inserted into the cavity 16. A first positioning post 68 extends from the outer surface of the first plate 61, while a second positioning post 69 extends from the outer surface of the second plate 62. The two positioning posts 68 and 69 locate the calibration device 60 longitudinally within the cavity 16 by abutting the end plate 15 and the main body end wall 54, respectively.

A calibration standard 70 is mounted centrally between the two calibration device plates 61 and 62 and the vanes 63. In the preferred embodiment, the calibration standard 70 is a rectangular solid with a square cross section in a plane parallel to plates 61 and 62. When the calibration device 60 is inserted into the turbidimeter 10 the flat surfaces of the calibration standard 70 are orthogonal to the radial axes on which the light emitters and detectors 41-44 are mounted. Due to its square cross sectional shape, the calibration standard 70 has the same dimension along the first radial axis 51 between the first light emitter 41 and the first detector 43 as along the second radial axis 52 between the second emitter 42 and the second detector 44. Thus, the two light paths through the standard along these axes are the same. The calibration standard 70 is a glass ceramic composite. One example of a suitable glass ceramic composite is marketed under the trademark "Zerodur" by Schott Glaswerke of Mainz, West Germany. Such composites are formed by heat treating a glass block so that it becomes partially crystalline, i.e. the material has both a vitreous and a crystalline phase. Since the two phases have different indices of refraction, a given amount of light will be scattered as it passes through the standard 70. Thus, the calibration standard 70 can simulate a fluid having a defined turbidity.

Prior to using the calibration device 60, the equivalent turbidity of the standard 70 must be determined. To do so, the calibration device is placed in a reference turbidimeter that was previously calibrated by a conventional liquid primary standard introduced into the cavity 16. After the reference turbidimeter has been calibrated and drained, its baffle assembly 30 is removed and replaced by the calibration device 70. The reference turbidimeter then is sealed and operated to measure the turbidity simulated by the calibration standard 70.

Once the equivalent turbidity of the calibration device 60 is known, it can be used to calibrate other turbidimeters. The calibration device is placed in the cavity of another turbidimeter and its control circuitry is adjusted until the measured turbidity coincides which the turbidity simulated by the calibration standard 70. Following this process, the calibration device 60 is removed and the baffle assembly 30 is inserted into the cavity which then is sealed by the end cap and plate 14 and 16 so that the device may be placed in operation.

We claim:

1. An apparatus for measuring turbidity of a fluid comprising:
    a housing having a cavity with upper and lower regions, an inlet through which the fluid enters the lower region of the cavity, and an outlet through which the fluid exits the upper region of the cavity;
    a baffle assembly within the cavity and having a first means for directing substantially all the fluid from the inlet into the upper region, a second means for directing fluid with entrained gas through the upper region to the outlet, a third means for directing fluid substantially devoid of entrained gas through a turbidity sensing zone in the cavity; and
    means for measuring the turbidity of the fluid flowing in the sensing zone.

2. The apparatus as recited in claim 1 wherein the first means of said baffle assembly comprises a first wall extending across the lower region of the cavity and defining a passage in the upper region for the fluid to flow from one side of the first wall to another side.

3. The apparatus as recited in claim 1 wherein said baffle assembly further comprises a second wall spaced from said first wall and extending across substantially the entire cavity in both the upper and lower regions; wherein the second means of said baffle assembly comprises a first passage in the upper region for the fluid to flow from one side of the second wall to another side; and the third means of said baffle assembly comprises a second passage in the lower region for the fluid to flow from one side of the second wall to another side.

4. The apparatus as recited in claim 3 wherein the first passage at its narrowest section has a smaller cross sectional area than a cross sectional area of the second passage at the latter passage's narrowest section.

5. The apparatus as recited in claim 1 wherein said baffle assembly comprises first, second and third walls within the cavity between the inlet and outlet;
    the first wall forming the first means for directing by extending across the lower region of the cavity and defining a first passage in the upper region through which the fluid flows from one side of the first wall to another side;
    the second wall spaced from said first wall and extending across substantially the entire cavity in both the upper and lower regions; and
    the third wall spaced from said second wall and extending across substantially the entire cavity in both the upper and lower regions;
    wherein the second means for directing fluid comprises a second passage in the upper region through which the fluid flows from one side of the second wall to another side and from from one side of the third wall to another side; and
    wherein the third means for directing fluid comprises a third passage in the lower region through which the fluid flows from one side of the second wall to another side, and a fourth passage through which the fluid flows from one side of the third wall to another side.

6. The apparatus as recited in claim 1 wherein said housing further includes:
    a first light emitter for producing a beam of light along a first line through the sensing zone in the cavity;
    a first light detector aligned along the first line with said first light emitter;
    a second light emitter for producing a beam of light along a second line through the sensing zone in the cavity; and
    a second light detector aligned along the second line with said second light emitter;
    wherein the second line is transverse to the first line.

7. The apparatus as recited in claim 6 wherein said baffle assembly further includes a first member which blocks light from traveling in a straight line from said first light emitter to said second light detector; and a second member which blocks light from traveling in a straight line from said second light emitter to said first light detector.

8. The apparatus as recited in claim 7 wherein said baffle assembly further includes a third member which blocks light that is reflected by one of said first and second light detector from traveling in a straight line to the other of said first and second light detectors.

9. The apparatus as recited in claim 1 wherein said baffle assembly is removable from the cavity.

10. The apparatus as recited in claim 9 wherein said housing further includes a means that engages and restricts movement of said assembly when fluid flows through the cavity.

11. The apparatus as recited in claim 9 further comprising a calibration device for insertion in the cavity when said baffle assembly is removed, said calibration device including a body of a glass ceramic composite material which becomes positioned in the sensing zone when said calibration device is inserted in the cavity.

12. An apparatus for measuring turbidity of a fluid comprising:
    a housing having a cavity with an inlet and an outlet through which the fluid respectively flows into and out of said housing, the cavity having upper and lower regions;
    first, second and third vertically extending walls spaced from one another within the cavity of said housing, thereby forming a first cavity section on one side of said first wall with the inlet opening into the first cavity section, a second cavity section on another side of said first wall and between the first and second walls, a third cavity section between the second and third walls, and a fourth cavity section on an opposite side of said third wall from the third cavity section with the outlet communicating with the fourth cavity section;
    said first wall defining a first passage in the upper region through which substantially all the fluid flows between the first and second cavity sections;
    said second wall defining a second passage in the upper region between the second and third cavity sections, and a third passage between the second and third cavity sections in the lower region;
    said third wall defining a fourth passage in the upper region between the third and fourth cavity sections, and defining a fifth passage between the third and fourth cavity sections in the lower region; and
    means for measuring the turbidity of the fluid flowing in the third cavity section.

13. The apparatus as recited in claim 12 wherein the second passage at its narrowest section is wider than the third passage's narrowest section.

14. The apparatus as recited in claim 12 wherein said housing further includes:

a first light emitter for producing a beam of light along a first line through the third cavity section;

a first light detector aligned along the first line with said first light emitter;

a second light emitter for producing a beam of light along a second line through the third cavity section; and a second light detector aligned along the second line with said second light emitter;

wherein the second line is transverse to the first line.

15. The apparatus as recited in claim 14 further comprising a first member located between the second and third walls for preventing light from traveling in a straight line from said first light emitter to said second light detector; and a second member located between the second and third walls for preventing light from traveling in a straight line from said second light emitter to said first light detector.

16. The apparatus as recited in claim 15 further comprising a third member located between the second and third walls for preventing light from traveling in a straight line between said first and second light detectors.

17. In an apparatus for measuring turbidity of a fluid which includes a housing having a cavity through which the fluid flows, means for emitting a beam of light through the cavity, means for sensing a magnitude of light transmitted through the cavity, and means for producing a signal corresponding to the turbidity of the fluid in response to the magnitude of the light; the improvement comprising:

a device for calibrating the means for producing a signal, which device includes a block of glass ceramic material for placement in the beam of light passing through the cavity.

18. The apparatus as recited in claim 17 wherein:

the means for emitting includes a first light emitter for producing a beam of light along a first line through the cavity and a second light emitter for producing a beam of light along a second line through the cavity;

the means for sensing includes a first light detector aligned along the first line with said first light emitter and a second light detector aligned along the second line with said second light emitter; and said device for calibrating further comprises a first member for preventing light from traveling in a straight line from said first light emitter to said second light detector, and a second member for preventing light from traveling in a straight line from said second light emitter to said first light detector.

19. The apparatus as recited in claim 18 wherein said device for calibrating further comprises a third member for preventing light from traveling in a straight line between said first and second light detectors.

20. The apparatus as recited in claim 17 wherein said device for calibrating further comprises:

first and second planar members with said block being located therebetween;

a first vane extending between said first and second planar members at a position for blocking light from traveling in a straight line between said first light emitter and said second light detector;

a second vane extending between said first and second planar members at a position for blocking light from traveling in a straight line between said second light emitter and said first light detector; and third vane extending between said first and second planar members at a position for blocking light from traveling in a straight line between said first and second light detectors.

21. The apparatus as recited in claim 17 wherein:

the means for emitting includes a first light emitter for producing a beam of light along a first line through the cavity and a second light emitter for producing a beam of light along a second line through the cavity; and when said block of glass ceramic material is positioned in the cavity both the first and second lines intersect said block for substantially equal distances.

22. A method for calibrating a turbidimeter which includes a housing having a cavity, means for emitting a beam of light through the cavity, means for sensing a magnitude of light transmitted through the cavity, and means, responsive to the magnitude of the light, for producing a signal corresponding to a turbidity of a material in the cavity; said method comprising the steps of:

placing a body of glass ceramic material, which has a predefined equivalent turbidity, into the cavity;

operating the turbidimeter to produce the signal; and adjusting the means for producing a signal until the signal corresponds to the predefined equivalent turbidity.

* * * * *